United States Patent [19]

Liepmann et al.

[11] Patent Number: 4,594,436
[45] Date of Patent: Jun. 10, 1986

[54] ISOMERIC 2-CHLOROMETHYL-1,4-BENZODIAZEPINE OR 3-CHLORO-1,5-BENZODIAZOCINE COMPOUND

[75] Inventors: Hans Liepmann; Michael Ruhland, both of Hanover; Herbert Muesch, Wennigsen; Werner Benson, Hanover; Henning Heinemann, Hanover; Horst Zeugner, Hanover, all of Fed. Rep. of Germany

[73] Assignee: Kali-Chemie Pharma GmbH, Hanover, Fed. Rep. of Germany

[21] Appl. No.: 707,037

[22] Filed: Mar. 1, 1985

Related U.S. Application Data

[62] Division of Ser. No. 453,785, Dec. 27, 1982, Pat. No. 4,508,716.

[30] Foreign Application Priority Data

Dec. 28, 1981 [DE] Fed. Rep. of Germany ....... 3151597

[51] Int. Cl.[4] .................. C07D 319/08; C07D 487/04; C07D 498/04; A61K 31/495
[52] U.S. Cl. .............................. 549/359; 260/239.3 D; 260/243.3; 260/244.4; 260/245.7; 260/330.3; 260/330.9; 514/219; 514/220; 514/250; 514/339; 514/422; 514/453; 514/461; 514/463; 544/343; 544/346; 546/271; 548/518; 549/59; 549/433; 549/472
[58] Field of Search ............... 260/244.4, 245.7, 330.3, 260/330.9; 549/59, 472, 359, 433

[56] References Cited

U.S. PATENT DOCUMENTS

| | | | |
|---|---|---|---|
| 3,403,161 | 9/1968 | Fryer | 260/239 BD |
| 3,846,443 | 11/1974 | Moffett | 260/239 BD |
| 3,933,816 | 1/1976 | Szmuszkovicz | 260/247.5 |
| 3,998,809 | 12/1976 | Mikowski et al. | 260/239 BD |
| 4,073,784 | 2/1978 | Moffett | 260/243.3 |
| 4,096,141 | 6/1978 | Milkowski et al. | 260/239 BD |
| 4,098,786 | 7/1978 | Milkowski et al. | 260/239 BD |
| 4,325,957 | 4/1982 | Zeugner et al. | 260/244.4 |
| 4,338,314 | 7/1982 | Liepmann et al. | 260/239 R |
| 4,508,716 | 4/1985 | Liepmann et al. | 260/239.3 D |

FOREIGN PATENT DOCUMENTS 8045 2/1980 European Pat. Off.
2314993 10/1974 Fed. Rep. of Germany.

OTHER PUBLICATIONS

Smith et al., J. Med. Chem. 1980, 23, 952–955.

*Primary Examiner*—Donald G. Daus
*Assistant Examiner*—Cecilia Shen
*Attorney, Agent, or Firm*—Schwartz, Jeffrey, Schwaab, Mack, Blumenthal & Evans

[57] ABSTRACT

[1,2]-fused 1,4-benzodiazepine compounds are disclosed corresponding to the general formula I

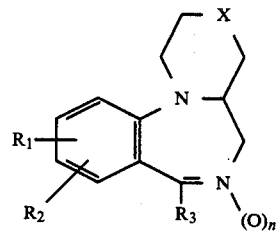

wherein X is an oxygen or sulfur atom or an optionally substituted imino group, $R_1$ is a hydrogen or halogen atom, lower alkyl radical, a lower alkoxy radical or a nitro group and $R_2$ is a hydrogen or halogen atom, a lower alkyl radical, a lower alkoxy radical or a nitro group, or if $R_1$ is a hydrogen atom, $R_2$ may also be a lower alkylthio radical, or, if $R_1$ is a hydrogen atom and X is a sulfur atom or an imino group, $R_2$ may be a trifluoromethyl radical; or $R_1$ and $R_2$ are bonded to adjacent carbon atoms and together denote a methylenedioxy or ethylenedioxy radical; $R_3$ is an optionally substituted furyl, thienyl, pyrrolyl or pyridyl radical and n is zero or, if $R_3$ is furyl or thienyl, n may be 0 or 1. The compounds may be in the form of their optical isomers or acid addition salts. The compounds exhibit neuroleptic properties. Processes for preparing the compounds and pharmaceutical compositions containing them are also disclosed.

1 Claim, No Drawings

ISOMERIC 2-CHLOROMETHYL-1,4-BENZODIAZEPINE OR 3-CHLORO-1,5-BENZODIAZOCINE COMPOUND

This is a division of application Ser. No. 453,785 filed Dec. 27, 1982, now U.S. Pat. No. 4,508,716.

BACKGROUND OF THE INVENTION

This invention relates to new [1,2]-fused 7-heteroaryl-1,4-benzodiazepine compounds and salts thereof, pharmaceutical compositions containing these compounds, and processes for the preparation of these compounds.

U.S. Pat. No. 4,338,314 discloses [1,2]-fused 7-phenyl-1,4-benzodiazepine derivatives which have a pronounced ulcer-inhibiting action and at the same time display only relatively little activity on the central nervous system.

It is the object of the invention to provide new [1,2]-fused 1,4-benzodiazepine compounds.

Another object of the invention is to provide new [1,2]-fused 1,4-benzodiazepine compounds which exhibit neuroleptic activity.

It is also an object of the present invention to provide new [1,2]-fused 1,4-benzodiazepine compounds which do not show strong central nervous system sedating activity.

A further object of the present invention is to provide new [1,2]-fused 1,4-benzodiazepine compounds which exhibit a good therapeutic range.

Yet another object of the present invention is to provide new [1,2]-fused 1,4-benzodiazepine compounds which exhibit low toxicity.

A still further object of the present invention is to provide pharmaceutical compositions comprising new [1,2]-fused 1,4-benzodiazepine compounds.

SUMMARY OF THE INVENTION

These and other objects are achieved according to one aspect of the present invention by providing a [1,2]-fused 1,4-benzodiazepine compound corresponding to the general formula I

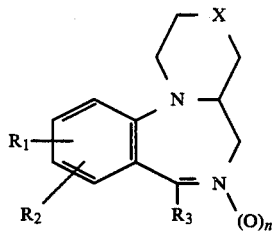

wherein

X represents an oxygen or sulfur atom or an imino group $=N-R_4$ in which $R_4$ represents a hydrogen atom, a $C_1-C_5$-alkyl radical, a $C_2-C_5$-alkyl radical which is terminally substituted by a methoxy radical or a hydroxyl group, a $C_3-C_5$-alkenyl radical or a cyclopropylmethyl radical;

$R_1$ represents a hydrogen or halogen atom, a lower alkyl radical, a lower alkoxy radical or a nitro group, and $R_2$ represets a hydrogen or halogen atom, a lower alkyl radical, a lower alkoxy radical or a nitro group, or, if $R_1$ is a hydrogen atom, $R_2$ may be a lower akylthio radical or, if $R_1$ is a hydrogen atom and X is a sulfur atom or an $=N-R_4$ group, $R_2$ may also be a trifluoromethyl radical; or $R_1$ and $R_2$ are bonded to adjacent carbon atoms and together denote a methylenedioxy or ethylenedioxy radical;

$R_3$ represents a radical selected from the group consisting of radicals corresponding to the formulas a, b, c or d

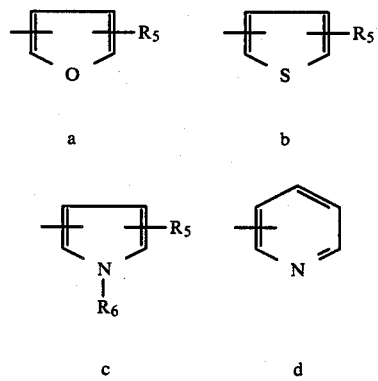

in which $R_5$ represents a hydrogen, fluorine, chlorine, or bromine atom, a lower alkyl radical or a nitro group and $R_6$ represents a hydrogen atom, a $C_1-C_5$-alkyl radical, a $C_2-C_5$-alkyl radical which is terminally substituted by a hydroxyl group or methoxy radical, a $C_3-C_5$-alkenyl radical or a cyclopropylmethyl radical; and n is zero or, if $R_3$ is the radical a or b, n is 0 or 1; and the optical isomers and acid addition salts of said compound.

If the substituents $R_1$ and $R_2$ in the compound of formula I represent or contain a lower alkyl group, this may be a straight-chain or branched alkyl group with peferably 1 to 4 carbon atoms, in particular a methyl or ethyl radical. Thus, preferred lower alkyl substituents are methyl radicals and preferred lower alkoxy or alkylthio substituents are methoxy or methylthio radicals, respectively. Suitable halogen atoms for the substituents $R_1$ and $R_2$ are, in particular, fluorine, chlorine and bromine atoms. The substituents $R_1$ and $R_2$ are preferably located in the 9- and/or 10-position, or, if they are nitro groups or trifluoromethyl radicals, in the 9-position, and are preferably selected from hydrogen, chlorine, bromine or fluorine atoms and methoxy and methyl radicals.

If X represents an $=N-R_4$ group and $R_4$ is an optionally substituted alkyl radical, this is preferably a straight-chain alkyl radical with 1 to 5, more preferably 1 to 3, carbon atoms. $R_4$ is preferably a methyl, ethyl, methoxyethyl or hydroxyethyl radical.

If $R_5$ is a lower alkyl radical, this can be straight-chain or branched and may contain 1 to 4 carbon atoms, and is preferably a methyl or ethyl radical.

If $R_3$ is a furyl group a, $R_5$ is preferably a hydrogen atom, a lower alkyl radical or a nitro group, more preferably a hydrogen atom or methyl radical.

If $R_3$ is a thienyl group b, $R_5$ is preferably a hydrogen atom or a lower alkyl radical, more preferably a methyl radical, a fluorine, chlorine or bromine atom or a nitro group.

If $R_3$ represents a pyrrolyl group c, $R_5$ is preferably a hydrogen atom or methyl radical. If $R_6$ is an optionally substituted alkyl radical, this is preferably straight-chain and contains 1 to 5, preferably 1 to 3, carbon atoms, and is more preferably a methyl, ethyl, methoxyethyl or hydroxyethyl radical, $R_6$ most preferably being a methyl radical. If X is an $=N-R_4$ group, $R_4$ and $R_6$ can advantageously be identical.

If $R_3$ is a pyridyl group d, this is preferably bonded in the 2-position to the benzodiazepine skeleton.

According to another aspect of the present invention, the objects are achieved by providing a process for the preparation of a new [1,2]-fused benzodiazepine compound corresponding to the general formula I and optical isomers and acid addition salts thereof, wherein (a) a compound corresponding to the general formula II or III

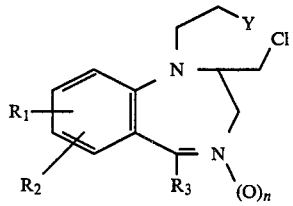

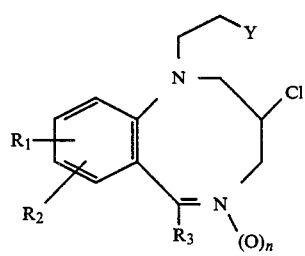

wherein $R_1$, $R_2$, $R_3$ and n have the above defined meanings and Y is a halogen atom, a lower alkanesulfonyloxy radical, a benzenesulfonyloxy radical, or a benzenesulfonyloxy radical in which the benzene ring is substituted by one or more lower alkyl radicals and/or halogen atoms, is reacted with an alkali metal hydroxide, an alkali metal sulfide or an amine of the formula $R_4-NH_2$, wherein $R_4$ has the above defined meaning; or (b) a compound of the formula Ib

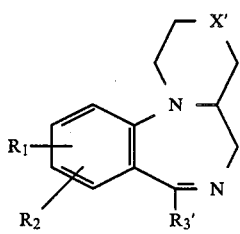

where $R_1$ and $R_2$ have the above defined meanings, $X'$ is an oxygen or sulfur atom and $R_3'$ is an a or b radical, is oxidized to form a compound of the formula Ia

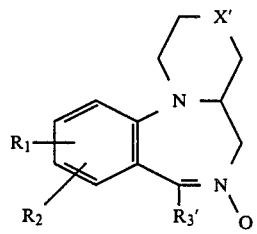

where $R_1$, $R_2$, $R_3'$ and $X'$ have the above defined meanings; or (c) a compound of the formula Id

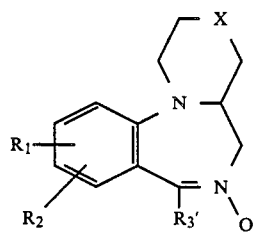

where $R_1$, $R_2$, $R_3'$ and X have the above defined meanings, is reduced to form a compound of the formula Ic

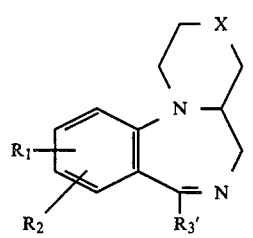

where $R_1$, $R_2$, $R_3'$ and X have the above defined meanings; or (d) a compound of the formula IV

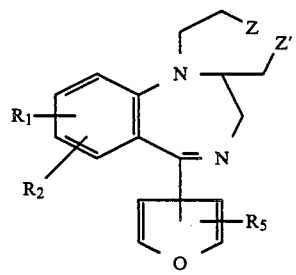

where $R_1$, $R_2$ and $R_5$ have the above defined meansings, Z has the meanings given above for Y and Z' is a chlorine atom, or Z and Z' together denote an oxygen or sulfur atom or an $=N-R_4$ group, is reacted with an amine of the formula $R_6-NH_2$, where $R_6$ has the above defined meaning, to form a compound of the formula Ie

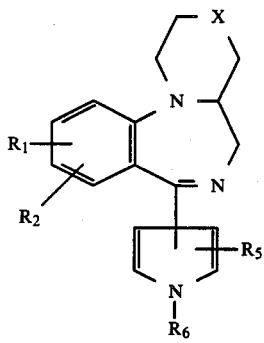

where $R_1$, $R_2$, $R_5$, $R_6$ and X have the above defined meanings. In a compound of formula I in which $R_1$ and/or $R_2$ is a hydrogen atom, the phenyl ring may be subsequently substituted with a chlorine or bromine atom, or, where $R_3$ is not a c radical, also with a nitro group. A racemic mixture of compounds of formula I may be ressolved into its optical isomers. Also it is considered within the scope of the invention to convert a free compound of formula I into an acid addition salt or an acid addition salt into the free compound of the formula I.

DETAILED DESCRIPTION OF PREFERRED EMBODIMENTS

It has now been found that the [1,2]-fused 7-heteroaryl-1,4-benzodiazepine compounds according to the invention have a novel pharmacological activity profile with a pronounced neuroleptic activity component, coupled with a good therapeutic range and a low toxicity.

The cyclization according to process step (a) above, can be carried out under the cyclization conditions described in U.S. Pat. No. 4,338,314 for the formation of [1,2]-fused benzodiazepine compounds. Starting compounds which can be employed are the 2-chloromethyl-1,4-benzodiazepine compounds of formula II, as well as the 3-chloro-1,5-benzodiazocine compounds of formula III or a mixture of benzodiazepines of formula II and corresponding benzodiazocines of formula III, since the benzodiazocine skeleton of the compounds of the formula III is converted into the benzodiazepine skeleton under the crystalization conditions. If Y is the compound of formula II and/or III is a halogen atom, this can be a chlorine, bromine or iodine atom, but is preferably a chlorine atom. If Y is a sulfonyloxy radical, it is preferably a toluenesulfonyloxy radical.

In order to prepare the fused oxazino-and thiazino-[4,3a] [1,4]benzodiazepine compounds of formula I (X=O or S), a compound of formula II and/or III is reacted with an alkali metal hydroxide or sulfide, for example with sodium hydroxide or sulfide or potassium hydroxide or sulfide. In order to prepare the fused pyrazino [1,2-a][1,4]-benzodiazepine compounds of formula I (X= =N—$R_4$), a compound of formula II and or III is reacted with an amine of the formula $R_4$—NH$_2$. The cyclizing reaction with the alkali metal hydroxide or sulfide or with the amine is advantageously carried out in a solvent which is inert under the reaction conditions, and at a temperature of from 50° to 150° C. Particularly suitable solvents for the cyclization are organic solvents, for example lower alcohols, such as methanol, ethanol and isopropanol; lower ketones, such as acetone; lower open-chain or cyclic ethers, such as diethyl ether, dioxane and tetrahydrofuran; pyridine, dimethylsulfoxide and dimethylformamide. The addition of water may be advantageous. If an amine $R_4$—NH$_2$ is used as the cyclizing agent, this amine can also be used as the solvent. In any case it is preferred that the cyclizing agent be used in excess. In the reaction of a compound of formula II and/or III, were $R_3$ is a furan radical and n is zero, with an amine $R_4$—NH$_2$, substantial replacement of oxygen by the =N—$R_4$ group takes place in the radical $R_3$ under the cyclization conditions at a temperature above 75° C., so that compounds of formula I where $R_3$ is a pyrrolyl radical are obtained as the main products. However, if the cyclizing reaction with the amine is carried out at a temperature below 75° C. or in the presence of a strong base, for example an inorganic base such as sodium hydroxide, such a replacement does not occur to any substantial extent, and the furan ring is retained.

N-Oxide compounds of formula Ia can also be obtained by oxidising compounds of formula Ib according to process step (b) in a manner which is known per se, to given the corresponding N-oxide. The oxidation can be carried out, for example, with an organic peracid in an organic solvent which is inert under the reaction conditions, for example by the process described in Chem. Rev. 68, 747 (1968). Particularly suitable oxidising agents are perbenzoic acids, such as, for example, 3-chloroperbenzoic acid. Examples of suitable solvents are halogenated hydrocarbons, such as methylene chloride.

Compounds of formula Ic can also be obtained by reducing the corresponding N-oxides of formula Id in a manner which is known per se [see, for example, J. Org. Chem. 26, 1,111 (1961)]. A particularly suitable reducing agent is phosphorus trichloride in an organic solvent which is inert under the reaction conditions, for example, a halogenated hydrocarbon, such as chloroform or methylene chloride. The preparation of a compound of formula I by reduction of the corresponding N-oxide is particularly suitable for the preparation of a 7-furyl-pyrazino[1,2-a] [1,4]benzodiazepine compound of formula I ($R_3$=a, X=N$R_4$). In the case where reduction is effected with phosphorus trichloride, chlorination in the furyl ring $R_3$ may take place to a slight extent, so that corresponding chlorinated compounds of formula I ($R_5$=Cl) may be obtained as by-products.

According to the process step (d), furyl compounds of formula I can be converted into pyrrole compounds of formula Ie by reaction with an amine $R_6$—NH$_2$. The conversion of the furyl radical into the pyrrolyl radical can be carried out at a temperature of from 80° to 150° C., under the cyclization conditions described for process step (a).

Subsequent substitution of the phenyl ring of the 1,4-benzodiazepine skeleton with halogen, or if $R_3$ does not represent pyrrolyl, with a nitro group, is possible in a manner which is known per se, both in the fused end products of formula I and at the stage of the cyclised intermediate products of formulas II and/or III. Examples of suitable halogenating agents include N-chlorosuccinimide and N-bromosuccinimide. The customary nitration reagents can be used to introduce the nitro group, for example potassium nitrate in sulphuric acid or, as a mild nitrating reagent, copper-II nitrate trihydrate in acetic anhydride.

If desired, a nitro group which may be present can also subsequently be converted into halogen atom or split off completely, in a manner which is known per se.

The compounds of formula I obtained by the present process can, in a manner which is known per se, be isolated in the form of the free bases or their acid addition salts and purified. Acid addition salts can be converted into the free bases in the customary manner, and, if desired, these can be converted into pharmacologically acceptable acid addition salts in a known manner. For this, for example, the acid desired as the salt component is added to a solution of a compound of formula I in a solvent. Organic solvents in which the corresponding salt is sparingly soluble are preferably chosen for the reaction. Examples of acids which are suitable for the formation of pharmacologically acceptable salts of compounds of formula I include inorganic acids, such as hydrochloric acid, sulphuric acid and phosphoric acid, or organic acids, for example organic sulphonic acids, such as methanesulphonic or toluenesulphonic acids or cyclohexylaminosulphonic acid, lower aliphatic carboxylic acids, which may be hydroxylated or can contain a double bond, such as lactic acid, succinic acid, tartaric acid, fumaric acid, maleic acid or citric acid, and aromatic lower carboxylic acids, such as benzoic acid.

In the synthesis of the compounds of formula I, the compounds are obtained in the form of their racemates. Both the racemic mixtures and the optically active forms of the compounds of formula I are thus included in the present invention. The racemic mixtures can be resolved to give optically active compounds in a manner which is known per se, by salt formation with suitable optically active acids, such as, for example, tartaric acid, and subsequent fractional crystallisation of the resulting salts into their optically active antipodes.

The benzodiazepine compounds of formula II and benzodiazocine compounds of formula III used as starting substances are novel. They can be prepared in a manner which is known per se, for example by the methods described in U.S. Pat. Nos. 3,998,809; 4,096,141; 4,098,786 and 4,244,869 and Canadian Pat. No. 1,112,980, the disclosures of which are incorporated herein by reference.

In particular, a 2-hydroxy-1,3-diaminopropane of formula V

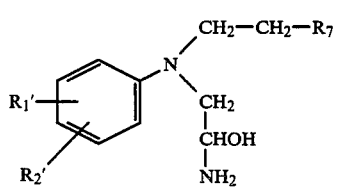

where $R_1'$ and $R_2'$ have the meanings given for $R_1$ and $R_2$, with the exception of the nitro group, and $R_7$ is a hydroxyl group or methoxy radical, can be acylated with an acyl chloride of the formula VI

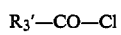  $R_3'—CO—Cl$     VI where $R_3'$ has the above defined meanings, to give an acylamine of the formula VII

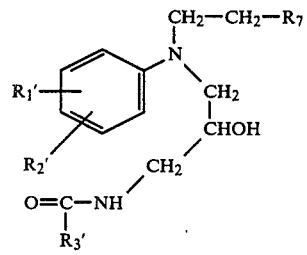

where $R_1'$, $R_2'$, $R_3'$ and $R_7$ have the above defined meanings, and the compound of formula VII can be subsequently cyclised in a manner which is known per se, by reaction with a phosphorous oxyhalide, preferably phosphorus oxychloride. For this reaction, the compound of formula VII or an acid addition salt thereof is advantageously treated with phosphorus oxychloride at a temperature of from 100° to 150° C., preferably at the boiling point of the reaction mixture, as described in German Offenlegungsschrift No. 2,520,937, thereby to form a mixture of two isomeric compounds of the formulae VIII and IX

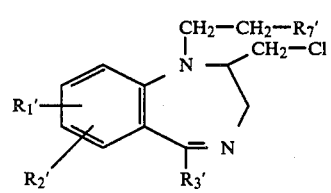

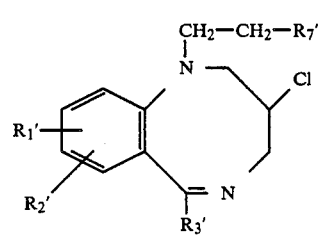

where $R_1'$, $R_2'$, and $R_3'$ have the above defined meanings and $R_7'$ is a chlorine atom or a methoxy radical.

If $R_7'$ represents a methoxy radical, this can be converted into the hydroxyl group in a manner which is known per se, by cleavage with hydriodic acid, and the hydroxyl group can then be esterified to a sulphonyl ester group Y or converted into a halogen atom Y, in a manner which is known per se. If desired, nitro groups can also be introduced into the phenyl part of the ring skeleton at this stage, in a manner which is known per se.

In the resulting mixture of the isomeric compounds of the formulae IIa and IIIa

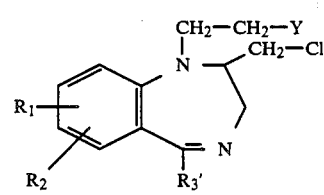

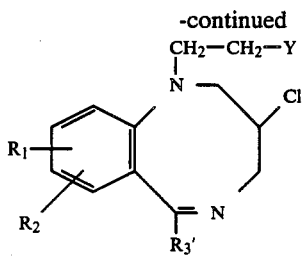
IIIa where $R_1$, $R_2$, $R_3'$ and Y have the above defined meanings, the two isomeric compounds are present in varying proportions, depending upon the nature of the substituents $R_1$, $R_2$ and $R_3'$. However, this is of no significance for the subsequent reaction of this mixture, since both isomers can be cyclised to form compounds of formula I in a uniform reaction. It is therefore not necessary to separate the isomer mixture before the further reaction. However, if desired, the isomers can of course also be separated at this stage and used individually for the subsequent reaction.

The compounds of formulas IIa and IIIa can be converted into the corresponding N-oxides in a manner which is known per se, for example under the conditions described above for process step (b).

In order to prepare compounds of formula II in which $R_3$ is a pyrrolyl radical, a compound of formula IIa where $R_3'$ is a furyl radical, is first converted into the corresponding dihydroxy compound of the formula X

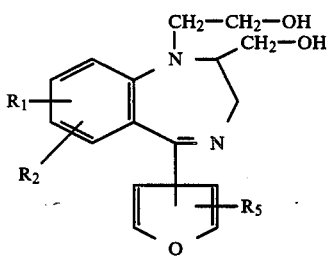
X where $R_1$, $R_2$ and $R_5$ have the above defined meanings, in a manner which is known per se, for example by a process analogous to that described in U.S. Pat. No. 4,098,786, and the hydroxy compound is then converted into the corresponding pyrrolyl compound of formula XI

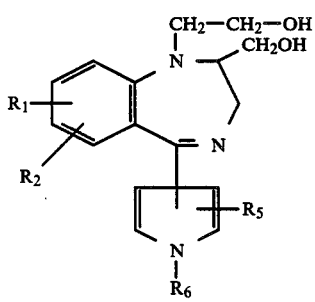
XI where $R_1$, $R_2$, $R_5$ and $R_6$ have the above defined meanings, by reaction with an amine $R_6$—$NH_2$, for example under the reaction conditions given for process step (d). The hydroxyl groups in the compound of formula XI can then be converted into chlorine atoms in a manner which is known per se, for example by treatment with phosphorus oxychloride or with triphenylphosphine/carbon tetrachloride.

In order to prepare a compound of formula II, it is also possible to use a 2-halobenzoyl compound of the formula XII

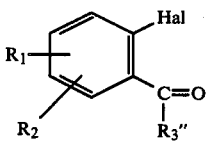
XII where $R_1$ and $R_2$ have the above defined meanings, $R_3''$ is an a, b or d radical and Hal denotes a halogen atom, preferably chlorine or fluorine, as the starting material. This is first reacted with a propanoldiamine compound of the formula XIII

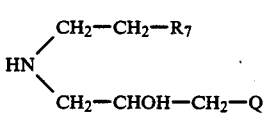
XIII where $R_7$ has the above defined meaning and Q is a radical which can be converted into an amino group, for example a protected amino group and subsequently the group Q is converted into the free amino group to form a compound of the formula XIV

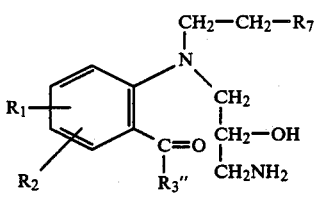
XIV where $R_1$, $R_2$ and $R_3''$ have the above defined meaning. The compound of formula XIV can be converted into a compound of formula II in a manner which is known per se, by cyclisation and subsequent conversion of the group $R_7$ into the group Y. This process is particularly suitable for the preparation of those compounds of formula II wherein the phenyl ring of the benzodiazepine skeleton contains a nitro group and wherein $R_3$ is a pyridyl radical.

In order to prepare a compound of formula II, it is also possible to start with a 2-aminobenzoyl compound of the formula XV

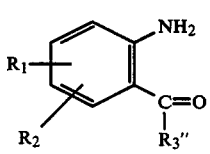
XV where $R_1$, $R_2$ and $R_3''$ have the above defined meanings. The amino group in such a compound is first monosubstituted by a $CH_2$—$CH_2$—$R_7$ radical, where $R_7$ has the above defined meaning, in a manner which is known per se, and is then reacted with 1,2-epoxypropylphthalimide by a method analogous to that described in Canadian Pat. No. 1,122,980. The phthalimide group in the resulting compound of formula XVI

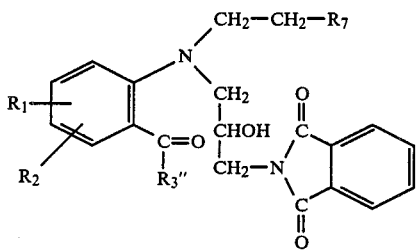

where $R_1$, $R_2$, $R_3''$ and $R_7$ have the above defined meanings, is then hydrolyzed in a manner which is known per se, and the resulting amino compound is cyclised to a benzodiazocine compound of the formula XVII

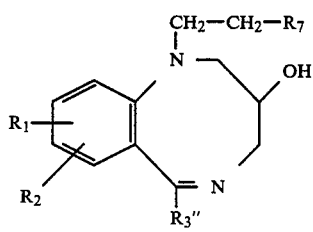

where $R_1$, $R_2$, $R_3''$ and $R_7$ have the above defined meanings, in an inert solvent, for example a lower alcohol such as methanol or acetic acid. The compound of formula XVII can be converted into the corresponding benzodiazepine compound of formula II by treatment with phosphorus oxychloride in a manner which is known per se.

The present heteroaryl-substituted 1,2-fused 1,4-benzodiazepine compounds and their pharmacologically acceptable acid addition salts have valuable pharmacological properties and exhibit a completely novel activity profile for 1,4-benzodiazepines.

Thus, they are distinguished from the phenyl-substituted 1,4-benzodiazepine compounds hitherto known, for example the ulcer-inhibiting compounds described in U.S. Pat. No. 4,338,314 or the 5-phenyl-1,4-benzodiazepin-2-ones known as minor tranquilizers such as diazepam or chlorodiazepoxide, in that they have a pronounced neuroleptic action component, while effects typical of tranquilizers are substantially suppressed. Thus, the present compounds display strong activities in pharmacological standard anaimal tests which are suitable for evaluating neuroleptic activities. For example, in mice, the compounds inhibit the apomorphine-induced (psychotic) climbing behaviour in a manner typical of neuroleptic agents. In contrast, the compounds of the invention exhibit greatly reduced central nervous system sedating properties, as can be shown in standard tests, for example by measuring the prolongation of the duration of hexobarbital anaesthesia in mice.

The neuroleptic 1,4-benzodiazepine derivatives according to the invention have only a low degree of sedating activity in the neuroleptically active dose range, and are distinguished by a low toxicity and a wide therapeutic range. On the basis of their advantageous activity profile, they are suitable for use in the treatment of illnesses of the schizophrenia type.

The novel activity profile of the present compounds can be seen from the results of the standard pharmacological tests on mice, which are described below.

DESCRIPTION OF THE PHARMACOLOGICAL TEST METHODS

1. Acute toxicity

The acute 7-day toxicity is determined following a single oral administration to white, fasting NMRl mice, and the $LD_{50}$ value is calculated by electronic data processing, by probit analysis.

2. Test for neuroleptic properties

Determination of the effective dose for inhibiting apomorphine-induced climbing behaviour in mice (modified method of P. Protais et al., Psychopharmacology 50, (1976), 1–6).

Groups each containing 10 male NMRl mice of 18–24 g. body weight are used per test dose. The test substance is administered perorally, as a suspension in 2% strength "Tylose" solution.

After 60 minutes, the animals are each injected subcutaneously with 1.0 mg./kg. of apomorphine, and immediately after the injection, each animal is placed under a vertical wire mesh cylinder (diameter 13 cm., height 16 cm., closed at the top). After 10, 20 and 30 minutes, the climbing behaviour of the animals is evaluated in accordance with the following point system:

0 points=no paw on the mesh 1 point=one or two paws touching the mesh 2 points=three or all paws gripping the mesh, or climbing For each test group, the sum of the points (maximum number of points=20) at the three test times is determined, and the average of the 3 values is taken for calculating the inhibition of climbing behaviour effected by the test substance.

In the table which follows, the inhibiting action is given in % inhibition in comparison with the climbing behaviour of a control group which was not treated with the test substance.

3. Test for the central nervous system sedating properties

Determination of the effective dose for prolonging hexobarbital anaesthesia in mice (modified methof of J. W. Kemp et al., Arch. Int. Pharmacology 193, (1971), 37–47).

Groups each containing 10 male mice of 22–26 g. body weight are used per test dose. The test substance is administered perorally as a suspension in 2% strength "Tylose" solution.

After 60 minutes, the animals are injected intravenously with 50 mg./kg. of hexobarbital sodium (=anaesthetic dose). The duration of the loss of the righting reflex in tenths of minutes is measured. The prolongation of this duration of the loss of reflex effected by the test substance is determined by comparison with the duration of the loss of reflex in control animals which have been treated with only "Tylose" solution free from test substance and with hexobarbital sodium. Table I, which follows gives the prolongation factor caused by the test substances.

Table I shows the results obtained by the test methods described above. The example numbers given for the compounds of formula I relate to the preparative examples described below.

TABLE I

| Test substance of the formula I Example No. | Inhibition of the apomorphine-induced climbing behaviour | | Prolongation of the duration of hexobarbital anaesthesia | | Toxicity LD$_{50}$ mg/kg |
| --- | --- | --- | --- | --- | --- |
| | Dose mg/kg | % inhibition | Dose mg/kg | Prolongation factor | |
| 22 | 8.1 | 50 | 37.7 | 1.5 | >811 |
| 35 | 9.8 | 35 | 9.8 | 2.1 | >311 |
| 10a | 13.3 | 31 | ≦42.2 | 0 | >422 |
| 36 | 22.3 | 34 | ≦70.4 | 0 | >701 |
| 63 | 21.3 | 11 | 67.2 | 1.5 | |
| 65 | 22.4 | 12 | | | |
| 9 | 4.2 | 48 | ≦41.5 | 0 | >893 |
| 41 | 13.9 | 14 | 43.8 | 1.6 | |
| 4 | 2.9 | 70 | ≦13.8 | 0 | ~440 |
| 51 | 2.2 | 57 | 22.3 | 1.9 | >704 |
| 55 | 0.2 | 47 | 6.8 | 1.3 | >315 |
| 69 | 0.7 | 71 | ≦28.0 | 0 | ~420 |
| 70 | 2.2 | 36 | ≦39.6 | 0 | ~790 |
| 74 | 3.3 | 70 | 33.0 | 2.0 | ~730 |

As medicaments, the compounds of formula I and their physiologically acceptable acid addition salts can be administered in pharmaceutical compositions together with customary solid or liquid pharmaceutical carriers or diluents. The dosage may vary depending on the species to be treated and the individual requirements. Parenteral formulations generally contain less active substance than products for oral administration. Examples of suitable pharmaceutical forms of presentation include tablets, capsules, powders, granules, dragees, solutions, emulsions, suspensions and suppositories. These forms of presentation can be prepared by methods which are known per se, using conventional pharmaceutical excipients and/or auxiliaries. Solid compositions may contain inorganic excipients, such as talc, or organic excipients, such as lactose or starch, and if appropriate other auxiliaries which are customary for producing tablets, such as, for example, lubricants, such as magnesium stearate, binders or tablet disintegrants. Liquid compositions may contain the customary diluents, such as water, liquid fatty oils or paraffin, and, if appropriate, other auxiliaries, for example suspending agents such as polyoxyethylene glycol, emulsifiers and the like.

The following non-limiting examples illustrate the preparation of the new compounds of general formula I.

The structures of the new compounds are confirmed by spectroscopic investigations, in particular by precise analysis of the NMR spectra. In the IR spectrum, the C=N band is determined in the range from 1,600 to 1,630 cm$^{-1}$. In the following Table 2 any amounts of water, acetone, ethanol or the like which may be bonded to salt forms are given.

EXAMPLE 1

1,2,4,4a-Tetrahydro-9-chloro-7-(3-thienyl)-5H-[1,4]oxazino[4,3-a][1,4]benzodiazepine A. A solution of 52 g of thiophene-3-carbonyl chloride in 200 ml of methylene chloride is added dropwise to a solution of 92 of N$_1$-(2-methoxyethyl)-N$_1$-(4-chlorophenyl)-2-hydroxy-1,3-diaminopropane and 40 g of triethylamine in 600 ml of methylene chloride at room temperature, and the reaction mixture is allowed to react for 15 hours. After the reaction mixture has been worked up, the reaction product is crystallized from isopropanol. 118 g of N$_1$-(3-thienylcarbonyl)-N$_2$-(2-methoxyethyl)-N$_2$-(4-chlorophenyl)-2-hydroxy-1,3-diaminopropane are obtained. Melting point: 141° to 142° C.

B. 10 ml of phosphorus oxychloride are added to 10 g of the compound described above and the mixture is left to react at 120° C. in an oil bath for 16 hours. The reaction mixture is then diluted with chloroform, and ice is subsequently added, followed by aqueous sodium hydroxide solution. After the organic phase has been worked up, the crude product is crystallised from ether. 8 g of 7-chloro-1-(β-chloroethyl)-2-chloromethyl-5-(3-thienyl)-2,3-dihydro-1H-1,4-benzodiazepine are obtained. Melting point: 115° to 116° C.

C. A solution of 11 g of 7-chloro-1-(β-chloroethyl)-2-chloromethyl-5-(3-thienyl)-2,3-dihydro-1H-1,4-benzodiazepine in 60 ml of dioxane and 160 ml of 4.5% strength sodium hydroxide solution is heated under reflux for 5 hours. After the solvent has been stripped off in vacuo, the reaction product is isolated from chloroform and is then chromatographed on aluminum oxide of activity level II, using methylene chloride. After the methylene chloride has been stripped off, 6.5 g of 1,2,4,4a-tetrahydro-9-chloro-7-(3-thienyl)-5H-[1,4]oxazino[4,3-a][1,4]benzodiazepine are obtained as an oil. This product is converted into its hydrochloride by reaction with alcoholic hydrogen chloride solution, and the product is crystallised as the hydrochloride.0.3H$_2$O from isopropanal. Melting point: 207° to 212° C.

EXAMPLE 2

1,2,4,4a-Tetrahydro-10-methoxy-7-(2-furyl)-5H-[1,4]oxazino[4,3-a][1,4]benzodiazepine. A. 100 g of N$_1$-(2-hydroxyethyl)-N$_1$-(3-methoxyphenyl)-2-hydroxy-1,3-diaminopropane in 800 ml of chloroform are reacted with 54.4 g of furan-2-carbonyl chloride in the presence of 45.8 g of triethylamine. After the reaction mixture has been worked up, the reaction product is crystallised from isopropanol. 120 g of N$_1$-(2-furylcarbonyl)-N$_2$-(2-hydroxyethyl)-N$_2$-(3-methoxyphenyl)-2-hydroxy-1,3-diaminopropane are obtained. Melting point 92° to 94° C.

B. 30 g of the above amide compound are left to react in 40 ml of phosphorus oxychloride in an oil bath at a bath temperature of 135° C. for 2 hours. The mixture is then diluted with chloroform and the solution is treated successively with ice and with sodium hydroxide solution. The organic phase is separated off and worked up. 25.4 g of an oily mixture are obtained, which contains about 20% of 9-methoxy-1-(β-chloroethyl)-3-chloro-6-(2-furyl)-1,2,3,4-tetrahydro-1,5-benzodiazocine and about 80% of 7-chloro-1-(β-chloroethyl)-2-chloromethyl-5-(2-furyl)-2,3-dihydro-1H-1,4-benzodiazepine. This mixture is used without further separation for the subsequent reaction. If desired, the benzodiazepine component of melting point 105° to 106° C. can be separatd off as crystals by crystallisation from ether.

C. A solution of 25 g of the isomeric mixture described above in 125 ml of dioxane and 325 ml of 4.5% strength sodium hydroxide solution is heated under reflux for 2 hours. After the solvent has been stripped off in vacuo, the reaction product is isolated from chloroform and is then chromatographed on aluminium oxide of activity level II, using methylene chloride. After the methylene chloride has been stripped off, the product is crystallised from ether. 6.7 g of 1,2,4,4a-tetrahydro-10-methoxy-7-(2-furyl)-5H-[1,4]oxazino[4,3-a][1,4]benzodiazepine are obtained. Melting point: 130° to 132° C.

EXAMPLE 3

1,2,4,4a-Tetrahydro-10-methoxy-7-(2-furyl)-5H-[1,4]oxazino[4,3a][1,4]benzodiazepine 6-oxide A solution of 6 g of 1,2,4,4a-tetrahydro-10-methoxy-7-(2-furyl)-5H-[1,4]oxazino[4,3-a][1,4]benzodiazepine (for the preparation, see Example 2) in 100 ml of methylene chloride is heated under reflux with 4.2 g of 3-chloroperbenzoic acid for 3 hours. The reaction solution is then rendered alkaline with aqueous dilute sodium hydroxide solution and is worked up in the customary manner. The crude product isolated is purified by chromatography on aluminum oxide of activity level II, using methylene chloride, and is crystallised from isopropanol. 2.3 g of 1,2,4,4a-tetrahydro-10-methoxy-7-(2-furyl)-5H-[1,4]oxazino[4,3-a][1,4]benzodiazepine 6-oxide are obtained. Melting point: 183° to 186° C.

EXAMPLE 4

1,2,3,4,4a,5-Hexahydro-3-methyl-7-(2-thienyl)-pyrazino-[1,2-a][1,4]benzodiazepine.

A. 170 g of $N_1$-(2-hydroxyethyl)-$N_1$-phenyl-2-hydroxy-1,3-diaminopropane are reacted with 118.7 g of thiophene-2-carbonyl chloride in the presence of 89 g of triethylamine in 800 ml of chloroform. After the reaction mixture has been worked up, the reaction product is crystallised from isopropanol. 190 g of $N_1$-(2-thienylcarbonyl)-$N_2$-(2-hydroxyethyl)-$N_2$-phenyl-2-hydroxy-1,3-diaminopropane are obtained. Melting point: 141° to 142° C.

B. 60 g of the above amide compound are left to react in 70 ml of phosphorus oxychloride in an oil bath at an oil bath temperature of 140° C. for 2 hours. The reaction mixture is then treated successively with ice and with sodium hydroxide solution and worked up in the customary manner and the reaction product is isolated from chloroform. 51.0 g of an oily mixture of about 90% of 1-(β-chloroethyl)-2-chloromethyl-5-(2-thienyl)-2,3-dihydro-1H-1,4-benzodiazepine and about 10% of 1-(β-chloroethyl)-3-chloro-6-(2-thienyl)-1,2,3,4-tetrahydro-1,5-benzodiazocine, which can be subsequently reacted without further purification, are obtained.

C. 20 g of the mixture described above in 300 ml of methanol are left to react with 20 g of methylamine at 95° C. in an autoclave for 14 hours. The reaction mixture is then worked up in the customary manner and the reaction product is purified by chromatography on aluminium oxide of activity level II, using methylene chloride/chloroform, and is then crystallised from ether. 12.8 g of 1,2,3,4,4a,5-hexahydro-3-methyl-7-(2-thienyl)-pyrazino[1,2a][1,4]benzodiazepine are obtained. Melting point: 124° to 125° C.

EXAMPLE 5

1,2,3,4,4a,5-Hexahydro-9-chloro-3-methyl-7-(2-furyl)-pyrazino[1,2-a][1,4]benzodiazepine 6-oxide.

A. 118.3 g of $N_1$-(2-methoxyethyl)-$N_1$-(4-chlorophenyl)-2-hydroxy-1,3-diaminopropane in 1,000 ml of chloroform are reacted with 61.0 g of furan-2-carbonyl chloride in the presence of 51.0 g of triethylamine. After the reaction solution has been worked up, the reaction product is crystallised from isopropanol. 147 g of $N_1$-(2-furylcarbonyl)-$N_2$-(2-methoxyethyl)-$N_2$-(4-chlorophenyl)-2-hydroxy-1,3-diaminopropane are obtained. Melting point: 121° to 123° C.

B. 146 g of the above amide compound are left to react in 150 ml of phosphorus oxychloride in an oil bath at an oil bath temperature of 120° C. for 4 hours, and the reaction mixture is then treated successively with ice and with aqueous sodium hydroxide solution and worked up. The reaction product is isolated from chloroform. 106.5 g of an oily mixture of 7-chloro-1-(β-chloroethyl)-2-chloromethyl-5-(2-furyl)-2,3-dihydro-1H-1,4; -benzodiazepine and 3,9-dichloro-1-(β-chloroethyl)-6-(2-furyl)-1,2,3,4-tetrahydro-1,5-benzodiazocine are obtained.

When the above mixture is treated with ether, 47.8 g of the above benzodiazepine compound of melting point 90° to 92° C. crystallise out.

43 g of a mixture of approximately equal parts of the benzodiazepine and the benzodiazocine isomers are obtained from the mother liquor after stripping off the solvent in vacuo and purifying the remaining residue on aluminium oxide of activity level II to III, using methylene chloride. This mixture is treated under reflux in 215 ml of tetrachloroethane for 1 hour. After the solvent has been stripped off in vacuo, the reaction product is treated with aqueous sodium hydroxide solution and purified again by chromatography on aluminium oxide, and is then crystallised from ether. A further 34 g of the benzodiazepine compound of melting point 92° to 94° C. are obtained.

C. A solution of 17.8 g of 7-chloro-1-(β-chloroethyl)-2-chloromethyl-5-(2-furyl)-2,3-dihydro-1H-1,4-benzodiazepine in 250 ml of methylene chloride is heated under reflux with 10.4 g of 3-chloroperbenzoic acid for 2-hours. The reaction solution is then rendered alkaline with aqueous dilute sodium hydroxide solution and is worked upon in the customary manner, and the reaction product is isolated and then purified by chromatography on aluminium oxide of activity level II, using methylene chloride, and crystallised from methanol. 13 g of 7-chloro-1-(β-chloroethyl)- 2-chloromethyl-5-(2-furyl)-2,3-dihydro-1H-1,4-benzodiazepine 4-oxide are obtained. Melting point: 158° to 159° C.

D. 12 g of the above N-oxide compound in 150 ml of methanol are left to react with 12 g of methylamine at 95° C. in an autoclave for 14 hours. After the reaction mixture has been worked up, the resulting crude product is purified by chromatography on aluminium oxide of activity level II, using methylene chloride/chloroform, and is crystallised from isopropanol. 7.3 g of 1,2,3,4,4a,5-hexahydro-9-chloro-3-methyl-7-(2-furyl)-pyrazino[1,2-a]-[1,4]benzodiazepine 6-oxide are obtained. Melting point: 202° to 204° C.

EXAMPLE 6

1,2,4,4a-Tetrahydro-9-chloro-7-(2-furyl)-5H-[1,4]thiazino[4,3-a][1,4]benzodiazepine.

8.5 g of disodium sulphide nonahydrate in 75 ml of water are added to a solution of 12.7 g of 7-chloro-1-(β-chloroethyl)-2-chloromethyl-5-(2-furyl)-2,3-dihydro-1H-1,4-benzodiazepine (or a mixture of this compound and the isomeric 3,9-dichloro-1-(β-chloroethyl)-6-(2-furyl)-1,2,3,4-tetrahydro-1,5-benzodiazocine (for the preparation see Example 5B) in 150 ml of dioxane, and the reaction mixture is heated under reflux for 5 hours. After the solvent has been stripped off in vacuo, the crude reaction product is isolated from chloroform and is then purified by chromatography on aluminium oxide of activity level II, using methylene chloride, and crystallised from ether. 9.7 g of 1,2,4,4a-tetrahydro-9-chloro-7-(2-furyl)-5H-[1,4]-thiazino[4,3-a][1,4]benzodiazepine are obtained. Melting point: 138° to 140° C.

EXAMPLE 7

1,2,3,4,4a,5-Hexahydro-9-chloro-3-methyl-7-(2-furyl)-pyrazino[1,2-a][1,4]benzodiazepine.

3.4 g of 7-chloro-1-(β-chloroethyl)-2-chloromethyl-5-(2-furyl)-2,3-dihydro-1H -1,4-benzodiazepine in 100 ml of methanol are left to react with 0.8 g of sodium hydroxide in 1 ml of water and 2.5 g of methylamine at 95° C. in an autoclave for 5 hours. The reaction mixture is then worked up in the customary manner and the reaction product is purified by chromatography on aluminium oxide of activity level II, using methylene chloride/chloroform, and the fractions containing the product of medium polarity are separated off and the 1,2,3,4,4a,5-hexahydro-9-chloro-3-methyl-7-(2-furyl)-pyrazino[1,2-a]-[1,4]benzodiazepine obtained therefrom is dissolved in isopropanol and converted into its salt with alcoholic hydrochloric acid. This salt crystallises from isopropanol as the dihydrochloride hemihydrate with 0.1 mol of isopropanol. Melting point: >240° C., yield: 0.8 g.

EXAMPLE 8

1,2,3,4,4a,5-Hexahydro-9-chloro-3-methyl-7-(2-furyl)-pyrazino[1,2-a][1,4]benzodiazepine 1 g of 7-chloro-1-(β-chloroethyl)-2-chloromethyl-5-(2-furyl)-2,3-dihydro-1H-1,4-benzodiazepine in 40 ml of methanol is left to react with 0.8 g of methylamine at 50° C. for 3 hours. The reaction mixture is then worked up as described in Example 7. On purification by chromatography, the fractions containing the more highly polar title compound are separated off. 0.4 g of 1,2,3,4,4a,5-hexahydro-9-chloro-3-methyl-7-(2-furyl)-pyrazino[1,2-a][1,4]benzodiazepine is obtained therefrom.

EXAMPLE 9

1,2,3,4,4a,5-Hexahydro-9-chloro-3-methyl-7-[2-(N-methyl)-pyrrolyl]-pyrazino[1,2-a][1,4]benzodiazepine 19 g of 7-chloro-1-(β-chloroethyl)-2-chloromethyl-5-(2-furyl)-2,3-dihydro-1H-1,4-benzodiazepine in 300 ml of methanol are left to react with 15 g of methylamine at 95° C. in an autoclave for 14 hours. After the reaction mixture has been worked up and the crude product has been purified by chromatography on aluminium oxide of activity level II, using methylene chloride/chloroform, the resulting 1,2,3,4,4a,5-hexahydro-9-chloro-3-methyl-7-[2-(N-methyl)-pyrrolyl]-pyrazino[1,2-a]8 1,4]benzodiazepine is converted into its salt in ethanol using ethanolic hydrochloric acid. This salt crystallises from ethanol/ether as the dihydrochloride with 0.75 mol of water. Melting point: >230° C., yield: 13.4 g.

EXAMPLE 10

(a)
1,2,3,4,4a,5-Hexahydro-3,9-dimethyl-7-(2-furyl)-pyrazino[1,2-a][1,4]benzodiazepine and

(b)
1,2,3,4,4a,5-Hexahydro-3,9-dimethyl-7-(5-chloro-2-furyl)-pyrazino[1,2-a][1,4]benzodiazepine 9.3 g of 1,2,3,4,4a,5-hexahydro-3,9-dimethyl-7-(2-furyl)-pyrazino[1,2-a][1,4]benzodiazepine 6-oxide (prepared analogously to Example 5) are heated under reflux in 150 ml of chloroform with 17 ml of phosphorus trichloride for 1 hour. The reaction mixture is then treated with aqueous sodium hydroxide solution and worked up. The resulting crude product is separated into its components by chromatography on aluminium oxide of activity level II, using methylene chloride/chloroform. 1.7 g of the less polar 1,2,3,4,4a,5-hexahydro-3,9-dimethyl-7-(5-chloro-2-furyl)-pyrazino[1,2-a][1,4]benzodiazepine are thereby initially obtained in the first fraction, and the product is isolated as an oil (IR: 1,615 cm$^{-1}$ C=N) (b). 5 g of the more highly polar 1,2,3,4,4a,5-hexahydro-3,9-dimethyl-7-(2-furyl)-pyrazino[1,2-a][1,4]benzodiazepine (a) are then obtained.

For conversion into its salt, the 1,2,3,4,4a,5-hexahydro-3,9-dimethyl-7-(2-furyl)-pyrazino[1,2-a][1,4]-benzodiazepine is treated, in isopropanol, with hydrogen chloride gas. The dihydrochloride trihydrate crystallises from isopropanol/ether. Melting point: 210° C. (decomposition).

EXAMPLE 11

1,2,3,4,4a,5-Hexahydro-9-nitro-3-methyl-7-(2-thienyl)-pyrazino[1,2a][1,4]benzodiazepine A. 12 g of copper-II nitrate trihydrate are added in portions to a solution of 15.5 g of 1-(β-chloroethyl)-2-chloromethyl-5-(2-thienyl)-2,3-dihydro-1H-1,4-benzodiazepine in 110 ml of acetic anhydride at 45° C. When the reaction has ended, ice-water is added to the reaction mixture, and the mixture is worked up under alkaline conditions. The reaction product is purified by chromatography on aluminium oxide of activity level II, using methylene choride. 7.3 g of 7-nitro-1-(β-chloroethyl)-2-chloromethyl-5-(2-thienyl)-2,3-dihydro-1H-1,4-benzodiazepine are obtained as an oil.

B. 2.7 g of the above compound in 100 ml of methanol are left to react with 10 g of methylamine at 95° C. in an autoclave for 14 hours. After the reaction mixture has been worked up, the reaction product is purified by chromatography on aluminium oxide of activity level II, using methylene chloride/chloroform, and is crystallised from ether. 1.1 g of 1,2,3,4,4a,5-hexahydro-9-nitro-3-methyl-7-(2-thienyl)-pyrazino[1,2a][1,4]benzodiaszepine are obtained. Melting point: 174° to 175° C.

EXAMPLE 12

1,2,3,4,4a,5-Hexahydro-3-n-butyl-9-methyl-7-(2-furyl)-pyrazino[1,2-a][1,4]benzodiazepine 6-oxide 4 g of 7-methyl-1-(β-chloroethyl)-2-chloromethyl-5-(2-furyl)-2,3-dihydro-1H-1,4-benzodiazepine 4-oxide (prepared analogously to Example 5A–C) are dissolved in 10 ml of n-butylamine and the solution is heated to 90° C. in an autoclave for 14 hours. After the reaction mixture has been worked up, the resulting crude product is purified by chromatography on aluminium oxide of activity level II, using methylene chloride/chloroform, and is crystallised from ether. 2.1 g of 1,2,3,4,4a,5-hexahydro-3-(n-butyl)-9-methyl-7-(2-furyl)-pyrazino[1,2-a][1,4]benzodiazepine 6-oxide are obtained. Melting point: 104° to 106° C.

EXAMPLE 13

1,2,4,4a-Tetrahydro-9-chloro-7-[2-(N-methyl)-pyrrolyl]-5H-[1,4]oxazino[4,3-a][1,4]benzodiazepine 2 g of 1,2,4,,4a-tetrahydro-9-chloro-7-(2-furyl)-5H-[1.4]oxazino[4,3-a][1,4]benzodiazepine (prepared analogously to Example 2) are heated to 95° C. with 1.8 g of methylamine hydrochloride and 4 g of methylamine in 100 ml of methanol in an autoclave for 4 hours. After the solvent has been stripped off, the crude product is isolated from chloroform and is then purified by chromatography on aluminium oxide of activity level II, using methylene chloride, and crystallised from hexane. 1.5 g of 1,2,4,4a-tetrahydro-9-chloro-7-[2-(N-methyl)-pyrrolyl]-5H-[1,4]oxazino[4,3-a][1,4]benzodiazepine are obtained. Melting point: 95° to 97° C.

EXAMPLE 14

1,2,4,4a-Tetrahydro-9,10-ethylenedioxy-7-(2-thienyl)-5H-[1,4]oxazino-[4,3-a][1,4]benzodiazepine A. 29.6 g of $N_1$-(2-thienylcarbonyl)-$N_2$-(2-hydroxyethyl)-$N_2$-(3,4-ethylenedioxyphenyl)-2-hydroxy-1,3-diaminopropane are left to react in 30 ml of phosphorus oxytrichloride in an oil bath at a bath temperature of 120° C. for 14 hours. The mixture is then diluted with chloroform, and the solution is treated successively with ice and with sodium hydroxide solution. The organic phase is separated off and worked up. The resulting reaction product solidifies after the solvent has been stripped off. Crystallisation from isopropanol gives 25.6 g of 7,8-ethylenedioxy-1-(β-chloroethyl)-2-chloromethyl-5-(2-thienyl)-2,3-dihydro-1H-1,4-benzodiazepine. Melting point: 184°–187° C.

B. A solution of 13 g of the product described above in 60 ml of dioxane is heated under reflux with 35 ml of 20% strength sodium hydroxide solution and 100 ml of water for 4 hours. After the solvent has been stripped off in vacuo, the reaction product is isolated from chloroform and is then chromatographed on aluminium oxide of activity level II, using methylene chloride. After the methylene chloride has been stripped off, the product is crystallised from ether. 5.5 g of 1,2,4,4a-tetrahydro-9,10-ethylenedioxy-7-(2-thienyl)-5H-[1,4]oxazino[4,3-a]-[1,4]benzodiazepine are obtained. Melting point: 192°–194° C.

The [1,2]-fused 7-heteroaryl-1,4-benzodiazepine compounds of the formula I listed in the table which follows were prepared by the processes described in Examples 1–14, starting from corresponding compounds of the formula II or III.

TABLE 2

| Example No. | $R_1$ | $R_2$ | $R_3$ | X | n | Salt | Melting point °C. |
|---|---|---|---|---|---|---|---|
| 15 | H | H | 2-thien. | O | 0 | Base | 160–162 |
| 16 | 9-Cl | H | 2-fur. | O | 0 | Base | 143–145 |
| 17 | 9-$C_2H_5O$ | H | 3-fur. | O | 0 | HCl | 224–226 |
| 18 | 9-$CH_3$ | H | 2-thien. | O | 0 | HCl.0.5$H_2O$ | 167–171 |
| 19 | 9-$CH_3$ | H | 2-fur. | O | 0 | Base | 129–131 |
| 20 | 9-$CH_3$ | H | 3-fur. | O | 1 | Base | 190–192 |
| 21 | 9-$CH_3$ | H | 3-fur. | O | 0 | Base | 121–122 |
| 22 | 9-$CH_3$ | H | 5-Br—2-thien. | O | 0 | Base | 117–120 |
| 23 | 10-$CH_3O$ | H | 2-fur. | S | 1 | Base | 154–156 |
| 24 | H | H | 2-thien. | S | 1 | Base | 188–191 |
| 25 | 9-$CH_3$ | H | 2-thien. | S | 0 | Base | 100–103 |
| 26 | 9-$CH_3$ | H | 2-fur. | S | 0 | Base | 128–130 |
| 27 | 9-$CH_3$ | H | 3-fur. | S | 0 | Base | 105–107 |
| 28 | 9-$CH_3$ | H | 5-Br—2-thien. | S | 0 | HCl | 205 (D) |
| 29 | H | H | 2-thien. | N—$CH_3$ | 1 | Base | 208–211 |
| 30 | 9-Cl | H | 2-thien. | N—$CH_3$ | 0 | Base | 115–117 |
| 31 | 9-Cl | H | 2-thien. | N—$CH_3$ | 1 | Base | 199–201 |
| 32 | 9-Cl | H | 3-thien. | N—$CH_3$ | 0 | 2HCl.0.5$H_2O$ | >240 |
| 33 | H | H | 2-thien. | N—H | 1 | Base | 204–206 |
| 34 | 9-$CH_3$ | H | 2-thien. | N—$CH_3$ | 0 | Base | 117–118 |
| 35 | 9-$CH_3$ | H | 2-fur. | N—$CH_3$ | 0 | Base | 182–184 |
| 36 | 10-$CH_3O$ | H | 2-fur. | N—$CH_3$ | 1 | Base | 189–191 |
| 37 | 9-$CH_3$ | H | N—$CH_3$—2-pyrrol. | N—$CH_3$ | 0 | Base | 93–95 |
| 38 | 9-$CH_3$ | H | N(—n-$C_4H_9$)—2-pyrrol. | N—n-$C_4H_9$ | 0 | Base | oil |
| 39 | 9-$CH_3$ | H | 5-Br—2-thien. | N—$CH_3$ | 0 | 2HCl.0,5$H_2O$.1(CH$_3$)$_2$CHOH | 200 (D) |
| 40 | 9-$NO_2$ | H | 2-thien. | N—$CH_3$ | 1 | Base | oil |
| 41 | 9-$C_2H_5O$ | H | N—$CH_3$—3-pyrrol. | N—$CH_3$ | 0 | 2HCl.1,5$H_2O$ | >240 |
| 42 | 9-$NO_2$ | H | 2-thien. | O | 0 | Base | oil |
| 43 | 11-$NO_2$ | H | 2-thien. | O | 0 | Base | 125–128 |
| 44 | H | H | 3-Cl—2-thien. | N—$CH_3$ | 0 | Base | 121–123 |
| 45 | H | H | 3-$CH_3$—2-thien. | N—$CH_3$ | 0 | 2 p-Tos. | 193–196 |
| 46 | 9-F | H | 2-thien. | N—$CH_3$ | 0 | 2HCl.1.5$H_2O$ | >240 |
| 47 | 10-$CH_3O$ | H | 2-fur. | N—$CH_3$ | 0 | Base | 121–122 |
| 48 | 10-$CH_3O$ | H | 2-fur. | NH | 1 | Base | 182–184 |
| 49 | 9-$C_2H_5O$ | H | 2-thien. | N—$CH_3$ | 0 | 2HCl | >240 |

TABLE 2-continued

| Example No. | R₁ | R₂ | R₃ | X | n | Salt | Melting point °C. |
|---|---|---|---|---|---|---|---|
| 50 | 9-CH₃S | H | 2-thien. | N—CH₃ | 0 | Base | 149–151 |
| 51 | 10-CH₃O | H | 2-thien. | N—CH₃ | 0 | Base | 126–128 |
| 52 | 9-(CH₃)₂CH | H | 2-thien. | N—CH₃ | 0 | Base | 169–170 |
| 53 | H | H | 2-thien. | NH | 0 | Base | 123–126 |
| 54 | 9,10-O—CH₂—O | | 2-thien. | N—CH₃ | 0 | Base.0.25H₂O | 217–219 |
| 55 | 10-F | H | 2-thien. | N—CH₃ | 0 | Base | 111–113 |
| 56 | H | H | 2-thien. | S | 0 | Base | 149–150 |
| 57 | H | H | N—CH₃—2-pyrrol. | N—CH₃ | 0 | Base | 149–152 |
| 58 | H | H | 5-CH₃—2-fur. | N—CH₃ | 1 | Base | 153–155 |
| 59 | 9,10-di-CH₃ | | 2-thien. | N—CH₃ | 0 | 2HCl.1.5H₂O | 230 (D) |
| 60 | H | H | 5-Cl—2-fur. | N—CH₃ | 1 | HCl | 230 (D) |
| 61 | H | H | 4-Br—2-thien. | N—CH₃ | 0 | Base | 139–140 |
| 62 | 10-CH₃ | H | 2-thien. | N—CH₃ | 0 | 2HCl.2H₂O. 0.2(CH₃)₂CHOH | 218 (D) |
| 63 | 10.8-di-CH₃ | | 2-thien. | O | 0 | Base | 144–147 |
| 64 | 10.8-di-CH₃ | | 2-thien. | N—CH₃ | 0 | 2HCl.1H₂O | >240 |
| 65 | 10.8-di-CH₃ | | 2-thien. | S | 0 | Base | 130–132 |
| 66 | 9-CF₃ | H | 2-thien. | N—CH₃ | 0 | | |
| 67 | H | H | 3-fur. | O | 0 | Base | 159–161 |
| 68 | 10.8-di-CH₃O | | 2-thien. | N—CH₃ | 0 | Base | 151–152 |
| 69 | H | H | 2-thien. | N—C₂H₅ | 0 | 2HCl.1,5H₂O | >240 |
| 70 | H | H | 2-thien. | N—CH₂—CH=CH₂ | 0 | 2HCl | >240 |
| 71 | H | H | 2-thien. | N—CH—(CH₃)₂ | 0 | 2HCl.1H₂O | 195 (S) |
| 72 | H | H | 2-thien. | N—C(CH₃)₃ | 0 | Base | 142–143 |
| 73 | H | H | 2-thien. | N—(n-C₄H₉) | 0 | Base | 140–141 |
| 74 | H | H | 2-thien. | N—(CH₂)₂CH(CH₃)₂ | 0 | 2HCl.H₂O. 0.66(CH₃)₂CHOH | 180 (S) |
| 75 | H | H | 2-thien. | N—CH₂—CH₂OCH₃ | 0 | Base | 71–73 |
| 76 | H | H | 2-thien. | N—(CH₂)₃OCH₃ | 0 | Base | 97–98 |
| 77 | H | H | 2-thien. | N—CH₂—CH₂OH | 0 | 2HCl.1.5H₂O | 185 (S) |
| 78 | H | H | 2-thien. | N—(CH₂)₃—OH | 0 | Base | 139–141 |
| 79 | H | H | N—[(CH₃)₃C—CH₂]—2-pyrrol. | O | 0 | Base | oil |
| 80 | H | H | N—(CH₃OCH₂—CH₂—CH₂) 2-pyrrol. | O | 0 | Base | 195–199 |
| 81 | H | H | 2-thien. | N—CH₂— | 0 | Base | 129–131 |
| 82 | 8,10-di-Cl | | 2-thien. | N—CH₃ | 0 | | |
| 83 | 9-(CH₃)₃C | H | 2-thien. | N—CH₃ | 0 | Base | 204–206 |
| 84 | 9-(CH₃)₃CO | H | 2-thien. | N—CH₃ | 0 | 2HCl | 240 |
| 85 | 9,10-OCH₂—CH₂—O | | 2-thien. | N—CH₃ | 0 | Base | 225–228 |
| 86 | 10-C₂H₅ | H | 2-thien. | N—CH₃ | 0 | Base | oil 114–116 |

—◁ = cyclopropyl
thien. = Thienyl,
fur. = Furyl,
pyrrol. = Pyrrolyl
HCl = Hydrochloride
Base = free base
p-Tos. = p-Toluenesulphonate
oil = oily,
D = decomposition,
S = sintering

EXAMPLE I

Tablets

Tablets having the following composition per tablet are prepared:

| 1,2,3,4,4a,5-Hexahydro-3-methyl-7-(2-thienyl)-pyrazino[1,2-a][1,4]benzodiazepine | 25 mg |
|---|---|
| Maize starch | 60 mg |
| Lactose | 130 mg |
| Gelatine (10% strength solution) | 6 mg |

The active compound, maize starch and lactose are made into a paste with the 10% strength gelatine solution. The paste is comminuted and the resulting granules are placed on a suitable metal sheet and dried at 45° C. The dried granules are passed through a comminuting machine and mixed with the further following auxiliaries in a mixer:

| Talc | 5 mg |
|---|---|
| Magnesium stearate | 5 mg |
| Maize starch | 9 mg | and the mixture is then pressed to tablets weighing 240 mg.

The foregoing description and examples have been set forth merely to illustrate the invention and are not intended to be limiting. Since modifications of the disclosed embodiments incorporating the spirit and substance of the invention may occur to persons skilled in the art, the scope of the invention is to be limited solely with respect to the appended claims and equivalents.

We claim:

1. A compound coresponding to the formula II or III

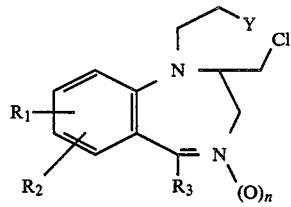  II

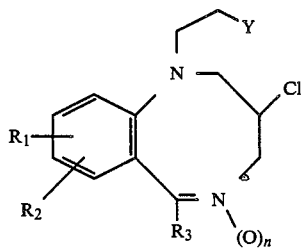  III wherein

R₁ represents a hydrogen or halogen atom, a lower alkyl group, a lower alkoxy group or a nitro group, and R₂ represents a hydrogen or halogen atom, a lower alkyl group, a lower alkoxy group or a nitro group, or, if R₁ is a hydrogen atom, R₂ may also be lower alkylthio group or a trifluoromethyl group; or R₁ and R₂ are bonded to adjacent carbon atoms and together denote a methylenedioxy or ethylenedioxy group;

R₃ represents a group selected from the group consisting of groups corresponding to the formulas a, b, c and d

a   b

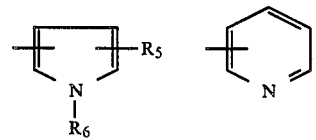

c   d in which R₅ is a hydrogen, fluorine, chlorine or bromine atom, a lower alkyl group or a nitro group and R₆ is a hydrogen atom, a C₁–C₅-alkyl group, a C₂–C₅-alkyl group which is terminally substituted by a hydroxyl group or a methoxy group, a C₃–C₅-alkenyl group or a cyclopropylmethyl group;

n is zero or, if R₃ is a group a or b, n is 0 or 1, and Y is a halogen atom, a lower alkanesulfonyloxy group, a benzenesulfonyloxy group or a benzenesulfonyloxy group in which the benzene ring is substituted by a lower alkyl group or halogen atom.

* * * * *